(12) United States Patent
McGuigan

(10) Patent No.: US 9,321,798 B2
(45) Date of Patent: Apr. 26, 2016

(54) PHOSPHORAMIDITE DERIVATIVES OF GEMCITABINE FOR USE IN THE TREATMENT OF CANCER

(75) Inventor: Christopher McGuigan, Cardiff (GB)

(73) Assignee: NuCana BioMed Limited, Camberley (GB)

(*) Notice: Subject to any disclaimer, the term of this patent is extended or adjusted under 35 U.S.C. 154(b) by 211 days.

(21) Appl. No.: 13/877,673

(22) PCT Filed: Oct. 5, 2011

(86) PCT No.: PCT/GB2011/001446
§ 371 (c)(1),
(2), (4) Date: Jun. 12, 2013

(87) PCT Pub. No.: WO2012/045999
PCT Pub. Date: Apr. 12, 2012

(65) Prior Publication Data
US 2013/0252918 A1    Sep. 26, 2013

(30) Foreign Application Priority Data

Oct. 6, 2010 (GB) .................................. 1016855.7

(51) Int. Cl.
| | | |
|---|---|---|
| A01N 43/04 | (2006.01) | |
| A61K 31/70 | (2006.01) | |
| C07H 19/04 | (2006.01) | |
| C07H 19/12 | (2006.01) | |
| C07H 19/10 | (2006.01) | |

(52) U.S. Cl.
CPC ...................................... *C07H 19/10* (2013.01)

(58) Field of Classification Search
CPC ........................................................ C07H 19/10
See application file for complete search history.

(56) References Cited

U.S. PATENT DOCUMENTS

| | | | |
|---|---|---|---|
| 6,573,247 B1 * | 6/2003 | McGuigan et al. ............. 514/43 |
| 7,951,787 B2 * | 5/2011 | McGuigan ...................... 514/49 |
| 8,263,575 B2 * | 9/2012 | McGuigan et al. ............. 514/47 |
| 8,551,965 B2 * | 10/2013 | McGuigan et al. ............. 514/43 |
| 8,658,616 B2 * | 2/2014 | McGuigan et al. ............. 514/47 |
| 8,877,731 B2 * | 11/2014 | Beigelman et al. ............. 514/45 |
| 8,933,053 B2 | 1/2015 | McGuigan et al. |

FOREIGN PATENT DOCUMENTS

| | | |
|---|---|---|
| DE | 277 463 | 4/1990 |
| DE | 279248 | 8/1996 |
| GB | 1 377 027 | 12/1974 |
| WO | WO 2005/012327 | 2/2005 |
| WO | WO2010/108140 | 9/2010 |
| WO | WO 2012/048013 | 4/2012 |

OTHER PUBLICATIONS

Cahard, D. et al, "Aryloxy Phosphoramidate Triesters as Pro-Tides," Mini-Reviews in Medicinal Chemistry, 2004, 4, pp. 371-382.

CAS Abstract accession No. 1995:297145 of Antiviral Chemistry & Chemotherapy, 1995, vol. 6(1), Nillroth et al., pp. 50-64.
CAS Abstract accession No. 1997:432895 of Drug Design and Discovery 1995 vol. 13 (1) Nillroth et al pp. 43-54.
English Abstract for DD279248 published Aug. 20, 1996, WPI Accession No. 1990-327965 [199044].
International Search Report issued in PCT/GB2011/001446 on Jan. 26, 2012.
Jones, B. C. et al, "Synthesis and anti-HIV activity of some novel phosphorodiamidate derivatives of 3'-asido-3'-deoxythymidine (AZT)," Antiviral Chemistry & Chemotherapy (1991) 2(1) pp. 35-39.
Nillroth et al, "The use of 5'-phosphate derivatives of nucleoside analogues as inhibitors of HIV-1 replication," Antiviral Chemistry & Chemotherapy 1995 vol. 6(1), pp. 50-64.
Nillroth et al, "Specific interaction between HIV-1 proteinase and 5'-phosphate peptidomimetic derivatives of nucleoside analogs," Drug Design and Discovery 1995 vol. 13(1), pp. 43-54.
UK Search Report issued in GB1016855.7 on Jan. 26, 2011.
Vail, D. M. et al, 2007 MCR Annual Meeting Los Angeles CA, "Efficacy and safety profile of GS-9219, a novel guanine nucleotide analog prodrug, for the treatment of lymphoid malignancies using pet dogs with spontaneous non-Hodgkin's lymphoma as a model," Apr. 18, 2007.
Wagner, C. R. et al, "Pronucleotides: Toward the In Vivo Delivery of Antiviral and Anticancer Nucleotides," Med. Res. Rev. 2000, 20, pp. 417-451.
McGuigan, Christopher M. et al., "Phosphorodiamidates as a Promising New Phosphate Prodrug Motif for Antiviral Drug Discovery: Application to Anti-HCV Agents", J. Med. Chem., 2011, 54 8632-8645.

(Continued)

*Primary Examiner* — Lawrence E Crane
(74) *Attorney, Agent, or Firm* — Fish & Richardson P.C.

(57) ABSTRACT

Phosphorodiamidate derivatives of e.g. gemcitabine are provided for use in treating cancer. In one embodiment, the two amidate motifs each comprises NR'R" where R' is H and R" is $CR_5R_6CO_2R_7$, where $R_6$ is H, $R_5$ is the side chain, including H and $C_1$, of a naturally occurring alpha amino acid, and $R_7$ is branched or unbranched, substituted or unsubstituted, acyclic or cyclic alkyl, including t-butyl-CH2-, benzyl and $C_3$ to $C_6$ cycloalkyl. Formula (I).

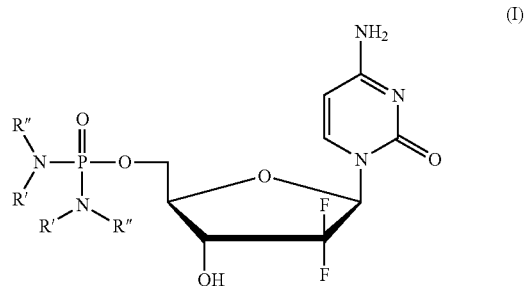

(I)

27 Claims, No Drawings

(56) References Cited

OTHER PUBLICATIONS

Gemzar Prescribing Label (18 pp) •GEMZAR, Highlights of Prescribing Information, Lilly USA, LLC, © 1996, revised Jun. 2014, 18 pages.

Search Results for Gemcitabine and Prostate Studies, ClinicalTrials.gov, retrieved on Mar. 24, 2015, http://clinicaltrials.gov/ct2/results?term=gemcitabine+and+prostate, 2 pages.

EPO Communication Pursuant to Article 94(3) EPC for European Patent Application No. 11 771 265.3 dated Sep. 17, 2014 (5 pp).

* cited by examiner

PHOSPHORAMIDITE DERIVATIVES OF GEMCITABINE FOR USE IN THE TREATMENT OF CANCER

CROSS REFERENCE TO RELATED APPLICATIONS

This application is a national phase entry under 35 U.S.C. §371 of PCT International Application No. PCT/GB2011/001446, filed Oct. 5, 2011, which claims the priority benefit of GB 1016855.7, filed Oct. 6, 2010.

The present invention relates to nucleotide derivatives and their use in the treatment of cancer.

The nucleoside analogue gemcitabine is well established as an anticancer agent. It functions as an inhibitor of DNA synthesis after activation to its 5'-phosphate form.

International patent application no. PCT/GB2004/003148 (publication no. WO 2005/012327 A) discloses the use of phosphoramidate drivatives of gemcitabine to treat cancer. The derivatives all have both an aromatic group linked through O to P and a single amidate group linking through N to P. Compared to gemcitabine, the derivatives may display an enhanced potency with respect to cancer and/or a reduced toxicity.

D M Vail et al, 2007 AACR Annual Meeting, Los Angeles, Calif. presented an efficacy and safety profile of a prodrug of the anti-proliferative nucleotide analog 9-(2-phosphonylmethoxyethyl) guanine used for the treatment of lymphoid malignancies. Guanine is derived from purine. The compound tested comprised a nucleoside phosphonate, i.e. a compound with a P—C link to the nucleoside base.

C R Wagner et al Med. Res. Rev. 2000, 20 417-451 discloses phosphoramidate diesters of FUdR and their use as anti-cancer agents.

Each of D Cahard et al, Mini-Reviews in Medicinal Chemistry, 2004, 4, 371-382 and B C Jones et al, Antiviral Chemistry & Chemotherapy (1991) 2(1), 35-39 discloses phosphorodiamidates of AZT and their use as anti-viral agents.

There is a need to provide compounds in the treatment of cancer that show improved properties, particularly having regard to enhanced potency and/or reduced cytotoxicity.

It is an object of the present invention to provide such compounds.

It is a further object of the present invention to provide such compounds for use in the treatment of cancer.

According to the present invention there is provided a chemical compound according to formula (I):

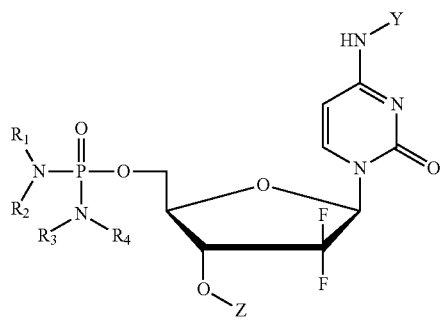

[I]

wherein:
$R_2$ is selected from the group comprising $CR_5R_6CO_2R_7$ and $C_1$-$C_6$alkyl and $R_1$ is selected from the group comprising H and $C_1$-$C_6$alkyl, or $R_1$ and $R_2$ together with the N atom to which they are attached form a ring moiety comprising 5 to 8 ring atoms;
$R_4$ is selected from the group comprising $CR_5R_6CO_2R_7$ and $C_1$-$C_6$alkyl and $R_3$ is selected from the group comprising H and $C_1$-$C_6$alkyl,
or $R_3$ and $R_4$ together with the N atom to which they are attached form a ring moiety comprising 5 to 8 ring atoms;
where, independently for each of $R_2$ and $R_4$:
  $R_5$ and $R_6$ are selected, independently, from the group comprising the side chains of naturally occurring alpha amino acids; and
  $R_7$ is selected from the group comprising $C_1$-$C_{18}$alkyl;
Y is selected from the group comprising H and C(O)R, where R is $C_1$-$C_{18}$alkyl;
Z is selected from the group comprising H and C(O)R, where R is $C_1$-$C_{18}$alkyl,
or a pharmaceutically acceptable derivative thereof.

Surprisingly, it has been found that phosphorodiamidate derivatives according to formula I are effective as potential chemotherapeutic agents in the treatment of cancer. Notably, compounds of formula (I) show enhanced anti-cancer potency and/or reduced cytotoxicity, compared to gemcitabine. The present invention thus provides the use of the compounds of the present invention in the treatment of cancer in *homo sapiens* and other mammals. In particular, compounds of the present invention are useful in the treatment of solid tumours, for example, in the treatment of colon cancer, breast cancer, pancreatic cancer, lung cancer and prostate cancer.

Although we do not wish to be bound by any theory, it is believed that in compounds of formula (I) it is the presence of the two amidate groups on the P atom, together with the identity of the groups $R_1$, $R_2$, $R_3$, $R_4$, $R_5$, $R_6$ and $R_7$, which contribute to the enhanced anti-cancer potency and/or the reduced cytotoxicity, compared to their nucleoside counterpart. Where $R_2$ and/or $R_4$ is the ester —$CR_5R_6CO_2R_7$, the anti-cancer potency exhibited varies with the choice of $R_5$, $R_6$ and, especially, $R_7$. Where $R_2$ and $R_4$ are each esters, the choice of each of $R_1$ and $R_3$, and where $R_2$ and/or $R_4$ is not an ester, the choice of the remaining $R_1$, $R_2$, $R_3$ and $R_4$ groups on the respective amino N atoms also contribute to the anti-cancer potency. In one embodiment, each of $R_2$ and $R_4$ is —$CR_5R_6CO_2R_7$ and each of $R_1$ and $R_3$ is H, especially in such an embodiment where each of $R_2$ and $R_4$ is —$CH_5R_6CO_2R_7$ and each of $R_1$ and $R_3$ is H, $R_2$ and $R_4$ are the same.

It will be appreciated that when $R_2$ and/or $R_4$ is the ester group —$CR_5R_6CO_2R_7$, the respective moieties —$NR_1$—$CR_5R_6CO_2$— and —$NR_3$—$CR_5R_6CO_2$— of the phosphorodiamidate compounds of formula (I) correspond to the structure of that of alpha amino acids.

$R_5$ and $R_6$ are selected, independently, from the group comprising the side chains of naturally occurring alpha amino acids. By "naturally occurring alpha amino acids" is meant Alanine, Arginine, Asparagine, Aspartic Acid, Cysteine, Cystine, Glycine, Glutamic Acid, Glutamine, Histidine, Hydroxylysine, Hydroxyproline, Isoleucine, Leucine, Lysine, Methionine, Phenylalanine, Proline, Serine, Threonine, Tryptophan, Tyrosine and Valine. The group comprising the side chains of these naturally occurring alpha amino acids, from which group $R_5$ and $R_6$ are independently selected, thus comprises the following moieties:

| | |
|---|---|
| $CH_3$— | as present in Alanine |
| $H_2NC(=NH)NH[CH_2]_3$— | as present in Argenine |
| $NH_2C(O)CH_2$— | as present in Aspargine |

-continued

| | |
|---|---|
| HO$_2$CH$_2$— | as present in Asparctic Acid |
| HSCH$_2$— | as present in Cysteine |
| HO$_2$CH(NH$_2$)CH$_2$SSCH$_2$— | as present in Cystine |
| H— | as present in Glycine |
| HO$_2$CH$_2$CH$_2$— | as present in Glutamic Acid |
| H$_2$N(O)CCH$_2$CH$_2$— | as present in Glutamine |
| C$_3$N$_2$HCH$_2$— | as present in Histidine |
| H$_2$NCH$_2$CH(OH)CH$_2$CH$_2$— | as present in Hydroxylysine |
| —CH$_2$CH(OH)CH$_2$— | as present in Hydroxyproline |
| CH$_3$CH$_2$CH(CH$_3$)— | as present in Isoleucine |
| (CH$_3$)$_2$CHCH$_2$— | as present in Leucine |
| H$_2$NCH$_2$(CH$_2$)$_3$— | as present in Lysine |
| CH$_3$SCH$_2$CH$_2$— | as present in Methionine |
| PhCH$_2$— | as present in Phenylalanine |
| —CH$_2$CH$_2$CH$_2$— | as present in Proline |
| OHCH$_2$— | as present in Serine |
| CH$_3$CH(OH)— | as present in Threonine |
| C$_8$NH$_6$CH$_2$— | as present in Tryptophan |
| HOC$_6$H$_4$CH$_2$— | as present in Tyrosine |
| (CH$_3$)$_2$CH— | as present in Valine. |

The term "a side chain of a naturally occurring alpha amino acid" thus includes H and moieties comprising only one C atom, as well as saturated, unbranched C$_3$ moieties attached additionally at their terminal C atom to their respective amino N atom, in which instance, for R$_2$, R$_1$ is absent and for R$_4$, R$_3$ is absent.

By "a pharmaceutically acceptable derivative" is meant any pharmaceutically acceptable salt, ester, salt of such ester, hydrate, solvate, or crystalline form or metabolite or any other compound which upon administration to a recipient is capable of providing (directly or indirectly) a compound of formula (I).

In one embodiment, R$_2$ and R$_4$ are the same.

In one embodiment, R$_2$ and R$_4$ are each —CR$_5$R$_6$CO$_2$R$_7$.

Suitably, R$_7$ is selected from the group comprising branched and unbranched C$_1$-C$_{18}$ acyclic alkyl and C$_3$-C$_8$ cyclic alkyl, any of which acyclic and cyclic alkyl moieties may be substituted, with generally one, two or three substituents as set out below, and/or unsaturated. In one embodiment, R$_7$ is a branched, saturated and unsubstituted acyclic alkyl group, examples of which include i-propyl and t-butyl-CH$_2$—. In one embodiment, R$_7$ is an unbranched acyclic alkyl group, examples of which include methyl and ethyl. In one embodiment, R$_7$ is a substituted acyclic alkyl group, an example of which is benzyl. In one embodiment, R$_7$ is C$_3$-C$_8$ cycloalkyl, an example of which is cyclohexyl. Suitably, R$_7$ comprises only HC. In one embodiment, R$_7$ is selected from the group comprising methyl, ethyl, i-propyl, t-butyl-CH$_2$—, benzyl and C$_3$-C$_6$ cycloalkyl. R$_7$ is especially t-butyl-CH$_2$—. Where R$_2$ and R$_4$ are both esters, suitably R$_7$ is the same in each of R$_2$ and R$_4$ and each of R$_1$ and R$_3$ is H.

In one embodiment, where R$_2$ and/or R$_4$ are the ester, R$_6$ is H and R$_5$ is selected from the group comprising the side chains of naturally occurring alpha amino acids, especially from among said side chains comprising only H or HC. In such an embodiment where R$_6$ is H, R$_5$ is especially selected from the group comprising H, methyl, i-propyl, —CH$_2$Ph, —CH$_2$CH(CH$_3$)$_2$ and —CH(CH$_3$)(C$_2$H$_5$). In such an embodiment where R$_6$ is H, R$_5$ is more especially methyl and, even more especially where R$_6$ is H and R$_5$ is methyl, R$_7$ is t-Bu-CH$_2$—. Where R$_2$ and R$_4$ are both esters, suitably R$_5$, R$_6$ and R$_7$ are the same in each of R$_3$ and R$_4$ and each of R$_1$ and R$_3$ is H.

Where R$_2$ and/or R$_4$ is the ester and R$_5$ differs from R$_6$, the stereochemistry of the amino acid may be D or L. In one embodiment the amino acid has natural L stereochemistry at *CR$_5$R$_6$. In another embodiment the amino acid has D stereochemistry at *CR$_5$R$_6$.

In one embodiment, where R$_2$ and/or R$_4$ is the ester, each of R$_5$ and R$_6$ is methyl.

In one embodiment, each of R$_1$ and R$_3$ is the same. Especially, each of R$_1$ and R$_3$ is H. Where each of R$_1$ and R$_3$ is H, each of R$_2$ and R$_4$ is especially CR$_5$R$_6$CO$_2$R$_7$. More especially, where each of R$_1$ and R$_3$ is H and each of R$_2$ and R$_4$ is CR$_5$R$_6$CO$_2$R$_7$, R$_6$ is H and R$_5$ is particularly selected from the group comprising H, methyl, i-propyl, —CH$_2$Ph, —CH$_2$CH(CH$_3$)$_2$, —CH$_2$(i-C$_3$H$_7$) and —CH(CH$_3$)(C$_2$H$_5$), even more particularly R$_5$ is methyl. Even more especially, in any of such embodiments R$_7$ is selected from the group comprising methyl, ethyl, i-propyl, t-butyl-CH$_2$—, benzyl and C$_3$-C$_6$ cycloalkyl, and especially is t-Bu-CH$_2$—. Especially where each of R$_1$ and R$_3$ is H, each of R$_2$ and R$_4$ is the same ester.

Where R$_1$ and R$_2$ together with the N amino atom to which they are attached form a ring moiety comprising 5 to 8 ring atoms and/or R$_3$ and R$_4$ together with the N amino atom to which they are attached form a ring moiety comprising 5 to 8 ring atoms, the ring atoms can include additional hetero atoms such as O and/or further N and/or the ring atoms may be substituted or unsubstituted and/or the ring may be saturated or unsaturated. Suitably, in any one ring, the ring atoms can comprise up to a total of four hetero atoms. Suitably, where substituted, there will generally be one, two or three substitutents present in any one ring. Substituents may any of: —CO$_2$R$_7$ (where R$_7$ is defined as set out above with respect to the moiety CR$_5$R$_6$CO$_2$R$_7$) and any of those moieties set out below as suitable substitutents having regard to alkyl groups present in compounds of formula I. Where either or both of the combination of R$_1$ and R$_2$ and the combination of R$_3$ and R$_4$, together with the respective N atoms to which they are attached, form a saturated five membered ring moiety comprising four carbon atoms and have at least the substituent —CO$_2$R$_7$ on the appropriate C atom adjacent the N atom, the respective groups —NR$_1$R$_2$ and/or —NR$_3$R$_4$ may correspond to those defined above for R$_1$, R$_2$, R$_3$ and R$_4$, respectively, where one or both of R$_5$ and R$_6$ comprises the side chain of proline or hydroxyproline.

In one embodiment of the compound of formula I, R$_1$ and R$_2$ together with the N atom to which they are attached form a ring moiety comprising 5 to 8 ring atoms and R$_3$ and R$_4$ together with the N atom to which they are attached form a ring moiety comprising 5 to 8 ring atoms: in any such embodiment such respective ring moieties are suitably the same and are as set out above.

If the phosphate centre is chiral, it may be mixed R and S, or enriched in one stereoisomer.

In one embodiment, Y is H.

In one embodiment, Z is H.

In one embodiment, each of Y and Z is H, in which embodiment a compound according to formula I has a base derived from gemcitabine.

Any of the above specifically recited features may be combined together, as set out in claim 1, to provide a compound of formula I of the present invention. In particular, where X and Z is each H so that the nucleoside base is derived from gemcitabine, each of the above recited embodiments of the diamidate motif is particularly suitably combined with the gemcitabine derived base moiety.

Particularly preferred compounds of the present invention include:

2'-Deoxy-2',2'-difluoro-D-cytidine-5'-O-bis(ethoxy-L-alaninyl)-phosphate;

2'-Deoxy-2',2'-difluoro-D-cytidine-5'-O-bis(benzoxy-L-alaninyl)-phosphate;

2'-Deoxy-2',2'-difluoro-D-cytidine-5'-O-bis(cyclohexoxy-L-alaninyl)-phosphate;

2'-Deoxy-2',2'-difluoro-D-cytidine-5'-O-bis(2,2-dimethyl-propoxy-L-alaninyl)-phosphate; and
2'-Deoxy-2',2'-difluoro-D-cytidine-5'-O-bis(iso-propoxy-L-alaninyl)-phosphate.

Reference in the present specification to an alkyl group means, unless otherwise stated, a branched or unbranched, cyclic or acyclic, saturated or unsaturated (e.g. alkenyl or alkynyl) hydrocarbyl radical. Where cyclic, the alkylene group is preferably $C_3$ to $C_{12}$, more preferably $C_5$ to $C_{10}$, more preferably $C_5$ to $C_7$. Where acyclic, the alkyl group is preferably $C_1$ to $C_{16}$, more preferably $C_1$ to $C_6$.

The alkyl groups may be substituted or unsubstituted. Where substituted, there will generally be one to three substituents present, preferably one substituent. Substituents may include halogen atoms, by which is meant F, Cl, Br and I atoms, and halomethyl groups such as $CF_3$ and $CCl_3$; oxygen containing groups such as oxo, hydroxy, carboxy, carboxy$C_{1-16}$alkyl, alkoxy, alkoyl, alkoyloxy, aryloxy, aryloyl and aryloyloxy; nitrogen containing groups such as amino, $C_{1-6}$alkylamino, di$C_{1-6}$alkylamino, cyano, azide and nitro; sulphur containing groups such as thiol, $C_{1-6}$alkylthiol, sulphonyl and sulphoxide; heterocyclic groups which may themselves be substituted; alkyl groups as defined above, which may themselves be substituted; and aryl groups, by which is meant aromatic groups containing 5 to 14 ring atoms, for example phenyl or naphthyl, and heteroaromatic groups containing one, two, three or four, preferably one, heteroatoms selected, independently, from the group consisting of O, N and S, for example pyridyl, pyrrolyl, furanyl and thiophenyl, which aryl groups themselves may be substituted. Substituents on said heterocyclic, alkyl and aryl groups are as defined immediately above.

Reference in the present specification to alkoxy and aryloxy groups means, respectively, alkyl-O— (for example where alkyl is $C_1$ to $C_{16}$, preferably $C_1$ to $C_6$) and aryl-O— (for example where aryl is a 5 to 14 membered aromatic mono- or bifused ring moiety, optionally containing 1, 2, 3 or 4 heteroatoms selected, independently, from O, S and N, preferably aryl is phenyl).

Reference in the present specification to alkoyl and aryloyl groups means, respectively, alkyl-CO— (for example where alkyl is $C_1$ to $C_{16}$, preferably $C_1$ to $C_6$) and aryl-CO— (for example where aryl is a 5 to 14 membered aromatic mono or bifused ring moiety, optionally containing 1, 2, 3 or 4 heteroatoms selected, independently, from O, S and N, preferably aryl is phenyl).

Reference in the present specification to alkoyloxy and aryloyloxy means, respectively, alkyl-CO—O— (for example where alkyl is $C_1$ to $C_{16}$, preferably $C_1$ to $C_6$) and aryl-CO—O— (for example where aryl is a 5 to 14 membered mono- or bifused aromatic ring system, optionally containing 1, 2, 3 or 4 heteroatoms selected, independently, from O, S and N, preferably aryl is phenyl).

Reference in the present specification to heterocyclic groups means groups containing one or more, pyrrolyl, imidazolyl, pyraziolyl, thiazolyl, isothiazolyl, oxazolyl, pyrrolidinyl, pyrrolinyl, imidazolidinyl, imidazolinyl, pyrazolidinyl, tetrahydrofuranyl, pyranyl, pyronly, pyridyl, pyrazinyl, pyridazinyl, piperidyl, piperazinyl, morpholinyl, thionaphthyl, benzofuranyl, isobenzofuryl, indolyl, oxyindolyl, isoindolyl, indazolyl, indolinyl, 7-azaindolyl, isoindazolyl, benzopyranyl, coumarinyl, isocoumarinyl, quinolyl, isoquinolyl, naphthridinyl, cinnolinyl, quinazolinyl, pyridopyridyl, benzoxazinyl, quinoxadinyl, chromenyl, chromanyl, isochromanyl and carbolinyl.

According to a further aspect of the present invention there is provided a compound having formula I according to the present invention for use in a method of treatment, preferably in the prophylaxis or treatment of cancer, particularly in the prophylaxis or treatment of solid tumours, for example, of any one of colon cancer, breast cancer, pancreatic cancer, lung cancer and prostate cancer.

According to a further aspect of the present invention there is provided a method of prophylaxis or treatment of cancer, particularly a method of prophylaxis or treatment of solid tumours, for example, of any one of colon cancer, breast cancer, pancreatic cancer, lung cancer and protate cancer, comprising administration to a patient in need of such treatment an effective dose of a compound having formula I according to the present invention.

According to a further aspect of the present invention there is provided use of a compound having formula I of the present invention in the manufacture of a medicament for use in the treatment or prophylaxis of cancer, particularly a medicament for use in the treatment or prophylaxis of solid tumours, for example, of any one of colon cancer, breast cancer, pancreatic cancer, lung cancer and prostate cancer.

According to a further aspect of the present invention there is provided a pharmaceutical composition comprising a compound having formula I of the present invention in combination with a pharmaceutically acceptable excipient, carrier or diluent.

According to a further aspect of the present invention there is provided a method of preparing a pharmaceutical composition comprising the step of combining a compound having formula I of the present invention with a pharmaceutically acceptable excipient, carrier or diluent.

According to a further aspect of the present invention there is provided a process for preparing a compound of formula I, the process comprising reacting with phosphoryl chloride ($POCl_3$) a compound of formula II,

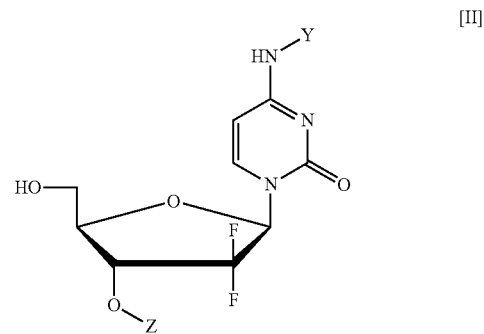

[II]

followed by reacting with amines of formulae $R_1R_2NH$ and $R_3R_4NH$,
wherein $R_1$, $R_2$, $R_3$, $R_4$, $R_5$, $R_6$, $R_7$, R, Z and Y have the meanings set out above.

The compound having formula I or pharmaceutical composition according to the present invention can be administered to a patient, which may be *homo sapiens* or animal, by any suitable means.

The medicaments employed in the present invention can be administered by oral or parenteral routes, including intravenous, intramuscular, intraperitoneal, subcutaneous, transdermal, airway (aerosol), rectal, vaginal and topical (including buccal and sublingual) administration.

For oral administration, the compounds of the invention will generally be provided in the form of tablets or capsules, as a powder or granules, or as an aqueous solution or suspension.

Tablets for oral use may include the active ingredient mixed with pharmaceutically acceptable excipients such as inert diluents, disintegrating agents, binding agents, lubricating agents, sweetening agents, flavouring agents, colouring agents and preservatives. Suitable inert diluents include sodium and calcium carbonate, sodium and calcium phosphate, and lactose, while cornstarch and alginic acid are suitable disintegrating agents. Binding agents may include starch and gelatin, while the lubricating agent, if present, will generally be magnesium stearate, stearic acid or talc. If desired, the tablets may be coated with a material such as glyceryl monostearate or glyceryl distearate, to delay absorption in the gastrointestinal tract.

Capsules for oral use include hard gelatin capsules in which the active ingredient is mixed with a solid diluent, and soft gelatin capsules wherein the active ingredient is mixed with water or an oil such as peanut oil, liquid paraffin or olive oil.

Formulations for rectal administration may be presented as a suppository with a suitable base comprising for example cocoa butter or a salicylate.

Formulations suitable for vaginal administration may be presented as pessaries, tampons, creams, gels, pastes, foams or spray formulations containing in addition to the active ingredient such carriers as are known in the art to be appropriate.

For intramuscular, intraperitoneal, subcutaneous and intravenous use, the compounds of the invention will generally be provided in sterile aqueous solutions or suspensions, buffered to an appropriate pH and isotonicity. Suitable aqueous vehicles include Ringer's solution and isotonic sodium chloride. Aqueous suspensions according to the invention may include suspending agents such as cellulose derivatives, sodium alginate, polyvinyl-pyrrolidone and gum tragacanth, and a wetting agent such as lecithin. Suitable preservatives for aqueous suspensions include ethyl and n-propyl p-hydroxybenzoate.

The compounds of the invention may also be presented as liposome formulations.

In general a suitable dose will be in the range of 0.1 to 300 mg per kilogram body weight of the recipient per day. A preferred lower dose is 0.5 mg per kilogram body weight of recipient per day, a more preferred lower dose is 6 mg per kilogram body weight of recipient per day, an even more preferred lower dose is 10 mg per kilogram body weight per recipient per day. A suitable dose is preferably in the range of 6 to 150 mg per kilogram body weight per day, and most preferably in the range of 15 to 100 mg per kilogram body weight per day. The desired dose is preferably presented as two, three, four, five or six or more sub-doses administered at appropriate intervals throughout the day. These sub-doses may be administered in unit dosage forms, for example, containing 10 to 1500 mg, preferably 20 to 1000 mg, and most preferably 50 to 700 mg of active ingredient per unit dosage form.

Embodiments of the present invention will now be described, by way of example only, with reference to the following examples, experimental procedures and experimental data.

Scheme 1 sets out a preparative pathway for preparing compounds of formula I. A person skilled in the art could use established synthetic methods to prepare close analogues related to the examples, by way of procedures disclosed in scheme 1.

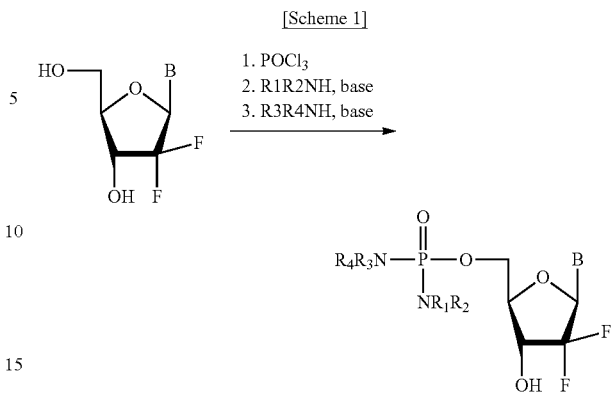

wherein B is a nucleic acid base as set out in claim 1, such as cytosine, and $R_1$, $R_2$, $R_3$ and $R_4$ have the meanings set out in claim 1.

To ease synthetic access the free 3'-OH in the nucleoside may be pre-protected, for example with a BOC group, and then deprotected after phosphoramidate construction, using standard methods.

The structure and purity of the compounds can most easily be established by P-31 NMR, but C-13 or H-1 NMR are also useful, as is HPLC and MS.

The compounds can be assayed by many in vitro or in vivo methods, but in the first instance a cell proliferation assay is rapid and informative. Many tumour cell lines can be used for the assay, we herein report typical data for target compounds in HRT18 colon tumour cell line, using standard MTT assay methods, typical in many laboratories.

EXAMPLES

Preparation of Gemcitabine Diamidates

Standard Procedure A: Synthesis of Diamidates

To a stirring solution of 3'-Boc-gemcitabine (1.0 eq.) suspended in triethylphosphate (1.0 ml), cooled to 0° C. POCl$_3$ (2.0 eq.) was added dropwise under Ar atmosphere. The resulting reaction mixture was stirred 16 h at 0°-4° C. The crude mixture was diluted with anhydrous DCM (10 mL) and appropriate amino acid ester (5.0 eq.) was added, followed by dropwise addition of DIPEA (10.0 eq) at −78° C. The reaction mixture was stirred for 96 h. The crude mixture was diluted with H$_2$O and extracted with DCM (6×20 mL). The organic phase were combined, dried under MgSO$_4$ and evaporated to yield a crude residue that was purified on silica gel using gradient of eluent (DCM/MeOH 99:1 to 97:3 to 95:5). (Excess of amino acid ester was removed by preparative TLC purification using DCM/MeOH 95/5 as an eluent).

Standard Procedure B: Synthesis of Diamidates

To a stirring solution of gemcitabine (1.0 eq.) suspended in triethylphosphate (1.0 ml), cooled to 0° C. POCl$_3$ (2.0 eq.) was added dropwise under Ar atmosphere. The resulting reaction mixture was stirred for 16 h at 0°-4° C. The crude mixture was diluted with anhydrous DCM (10 mL) and appropriate amino acid ester (5.0 eq.) was added, followed by dropwise addition of DIPEA (10.0 eq) at −78° C. The reaction mixture was stirred for 96 h under Ar atmosphere at 0°-4° C. The crude mixture was diluted with H$_2$O and extracted with DCM (6×20 mL). The organic phase were combined, dried under MgSO$_4$ and evaporated to yield a crude residue that was purified on silica gel using gradient of eluent (DCM/MeOH 99:1 to 97:3 to 95:5). (Excess of amino acid ester was removed by preparative TLC purification using DCM/MeOH 95/5 as an eluent).

Standard Procedure C: Deprotection of Boc Group

A mixture of 3'-Boc-protected diamidate in TFA/DCM (1:1) was stirred at 0° C. for 2 hours. The solvents were evaporated and the residues was treated with saturated NaHCO$_3$, and extracted with EtOAc. The organic layers were combined, dried (MgSO$_4$), filtered, reduced to dryness and purified on silica gel with gradient of eluent (DCM/MeOH 95:5 to 92:8).

2'-Deoxy-2',2'-difluoro-3'-(tert-butoxycarbonyloxy)-D-cytidine-5'-O-bis(ethoxy-L-alaninyl)] phosphate (1, MS151)

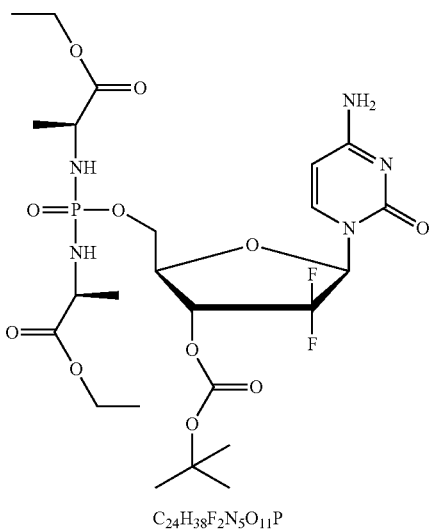

C$_{24}$H$_{38}$F$_2$N$_5$O$_{11}$P
Molecular Weight: 641.56 g/mol

Prepared according to the standard procedure A from 3'-Boc-Gemcitabine (0.20 g, 0.55 mmol), POCl$_3$ (0.17 g, 0.17 mL, 1.10 mmol), and (Et)$_3$PO (1.0 mL), followed by addition of L-Ala ethyl ester HCl salt (0.42 g, 2.75 mmol), DIPEA (0.71 g, 0.95 mL, 5.55 mmol). Column purification gave the product as a white solid (0.075 g, 21%).

$^{31}$P-NMR (MeOD, 202 MHz) δ 13.90

$^{19}$F-NMR (MeOD, 121 MHz) δ −115.35 (d, J=251 Hz), −119.19 (d, broad signal, J=249 Hz)

$^1$H-NMR (MeOD, 500 MHz) δ 7.71 (1H, d, J=8.16 Hz, H-base), 6.34 (1H, t, J=9.27 Hz, H-1'), 6.00 (1H, d, J=8.16 Hz, H-base), 5.27-5.22 (1H, m, H-3'), 4.37-4.33 (2H, m, 1×H-5', H-4'), 4.29-4.23 (1H, m, 1×H-5'), 4.22-4.16 (4H, m, 2×CH$_2$CH$_3$), 3.97-3.90 (2H, m, 2×CHCH$_3$), 1.52 (9H, s, C(CH$_3$)$_3$), 1.40 (6H, d, J=7.23 Hz, 2×CHCH$_3$), 1.28 (6H, apparent td, J=7.23 Hz, 2×CH$_2$CH$_3$)

$^{13}$C-NMR (MeOD, 125 MHz) δ 175.64 (d, $^3$J$_{C—P}$=5.70 Hz, C=O, ester), 167.76 (C=O, C—Ar, base), 157.60 (C—Ar, base), 153.18 (C=O, 3'-Boc), 143.02 (CH—Ar, base), 123.53 (apparent t, $^1$J$_{C—F}$=260 Hz, CF$_2$), 96.86 (CH—Ar, base), 86.20-85.81 (m, broad signal, C-1'), 85.19 (C(CH$_3$)$_3$), 78.82 (d, $^3$J$_{C—F}$=6.50 Hz, C-4'), 74.16, 73.84 (2×d, $^2$J$_{C—F}$=18.0 Hz, 17.53 Hz, C-3'), 64.45 (d, $^2$J$_{C—P}$=3.91 Hz, C-5'), 62.37 (CH$_2$CH$_3$), 51.10 (d, $^2$J$_{C—P}$=3.90 Hz, CHCH$_3$), 27.87 (C(CH$_3$)$_3$), 20.86, 20.75 (2×d, $^3$J$_{C—P}$=5.43 Hz, CHCH$_3$), 14.53 (CH$_2$CH$_3$)

MS (ES+) m/e: 664 (MNa$^+$, 100%), Accurate mass: C$_{24}$H$_{38}$F$_2$N$_5$O$_{11}$P required 641.56 found 642.24 (13%)

2'-Deoxy-2',2'-difluoro-D-cytidine-5'-O-bis(ethoxy-L-alaninyl)phosphate (2, CPF459)

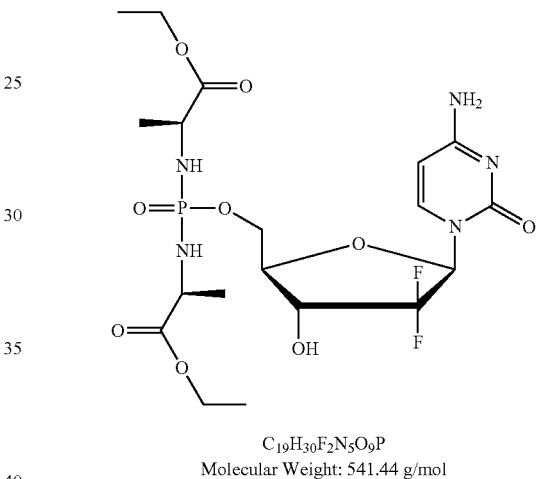

C$_{19}$H$_{30}$F$_2$N$_5$O$_9$P
Molecular Weight: 541.44 g/mol

Prepared according to the standard procedure C from the compound 1 (MS151) (0.075 g, 0.117 mmol), TFA/DCM (4 mL). Column purification followed by preparative TLC purification gave the product 2 as a white solid (7.0 mg, 11%).

$^{31}$P-NMR (MeOD, 202 MHz) δ 13.91

$^{19}$F-NMR (MeOD, 121 MHz) δ −118.39 (d, J=239 Hz), −119.83 (d, J=239 Hz)

$^1$H-NMR (MeOD, 500 MHz) δ 7.70 (1H, d, J=7.41 Hz, H-base), 6.29 (1H, t, J=8.35 Hz, H-1'), 6.01 (1H, d, J=7.41 Hz, H-base), 4.36-4.22 (3H, m, 2×H-5', H-3'), 4.19-4.17 (4H, m, 2×CH$_2$CH$_3$), 4.07-4.05 (1H, m, H-4'), 3.96-3.89 (2H, m, 2×CHCH$_3$), 1.40 (6H, d, J=7.23 Hz, 2×CHCH$_3$), 1.30-1.27 (6H, m, 2×CH$_2$CH$_3$)

$^{13}$C-NMR (MeOD, 125 MHz) δ 175.71 (d, $^3$J$_{C—P}$=4.15 Hz, C=O, ester), 167.70 (C=O, C—Ar, base), 157.79 (C—Ar, base), 142.67 (CH—Ar, base), 124.69 (apparent t, $^1$J$_{C—F}$=259 Hz, CF$_2$), 96.77 (CH—Ar, base), 86.15-85.80 (m, broad signal, C-1'), 80.40 (broad signal, C-4'), 71.32, 71.13 (2×d, $^2$J$_{C—F}$=22.80 Hz, C-3'), 64.38 (d, $^2$J$_{C—P}$=5.41 Hz, C-5'), 62.34 (CH$_2$CH$_3$), 51.10 (d, $^2$J$_{C—P}$=3.90 Hz, CHCH$_3$), 20.85, 20.70 (2×d, $^3$J$_{C—P}$=5.79 Hz, CHCH$_3$), 14.47 (CH$_2$CH$_3$)

HPLC$_b$ (H$_2$O/MeOH from 100/0 to 0/100 in 35 min) Rt 24.21 min

2'-Deoxy-2',2'-difluoro-D-cytidine-5'-O-bis(benzoxy-L-alaninyl)] phosphate (3, CPF457)

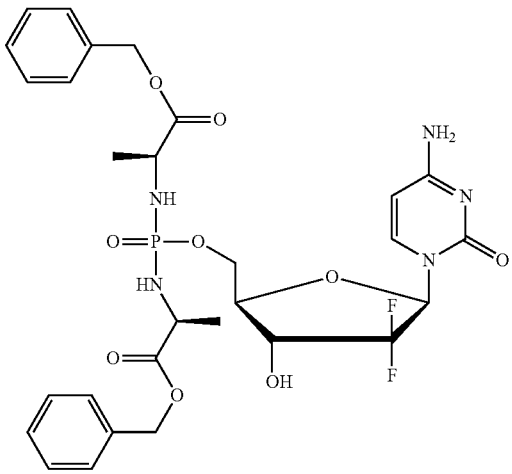

$C_{29}H_{34}F_2N_5O_9P$
Molecular Weight: 665.58 g/mol

Prepared according to the standard procedure B from Gemcitabine (0.25 g, 0.95 mmol), POCl$_3$ (0.29 g, 0.17 mL, 1.89 mmol), and (Et)$_3$PO (1.0 mL), followed by addition of L-Ala benzyl ester Ts salt (1.67 g, 4.75 mmol), DIPEA (1.23 g, 1.65 mL, 9.50 mmol). Column purification followed by preparative TLC purification gave the product 3 as a white solid (0.079 g, 12%).

$^{31}$P-NMR (MeOD, 202 MHz) δ 13.87

$^{19}$F-NMR (MeOD, 121 MHz) δ −118.14 (d, J=239 Hz), −119.70 (d, broad signal, J=239 Hz)

$^{1}$H-NMR (MeOD, 500 MHz) δ 7.67 (1H, d, J=7.53 Hz, H-base), 7.38-7.31 (10H, m, H—Ar), 6.27 (1H, t, J=8.05 Hz, H-1'), 5.97 (1H, d, J=7.51 Hz, H-base), 5.18-5.10 (4H, m, 2×CH$_2$Ph), 4.31-4.17 (3H, m, H-5', H-3', H-5'), 4.02-3.95 (3H, m, H-4', 2×CHCH$_3$), 1.38, 1.36 (6H, 2×d, J=7.14 Hz, 2×CHCH$_3$).

$^{13}$C-NMR (MeOD, 125 MHz) δ 175.43 (d, $^3J_{C—P}$=5.40 Hz, C=O, ester), 167.68 (C=O, C—Ar, base), 157.81 (C—Ar, base), 142.63 (CH—Ar, base), 137.29, 137.28 (C—Ar), 129.85, 129.66, 129.65, 129.40, 129.39, 129.32, 127.02 (CH—Ar), 123.69 (apparent t, $^1J_{C—F}$=258 Hz, CF$_2$), 96.87 (CH—Ar, base), 86.02 (apparent t, broad signal, $^2J_{C—F}$=27.0 Hz, C-1'), 80.46 (apparent t, $^3J_{C—F}$=8.20 Hz, C-4'), 71.28 (apparent t, $^2J_{C—F}$=23.44 Hz, C-3'), 68.00, 67.99 (CH$_2$Ph), 64.52 (d, $^2J_{C—P}$=4.78 Hz, C-5'), 51.15 (d, $^2J_{C—P}$=5.41 Hz, CHCH$_3$), 20.78, 20.67 (2×d, $^3J_{C—P}$=5.53 Hz, CHCH$_3$).

MS (ES+) m/e: 688.21 (MNa$^+$, 100%), Accurate mass: $C_{29}H_{34}F_2N_5O_9P$ required 665.58 found 666.22 (3%)

HPLC$_b$ (H$_2$O/MeOH from 100/0 to 0/100 in 35 min) Rt 24.15 min

2'-Deoxy-2',2'-difluoro-D-cytidine-5'-O-bis(cyclohexoxy-L-alaninyl)]-phosphate (4, CPF458)

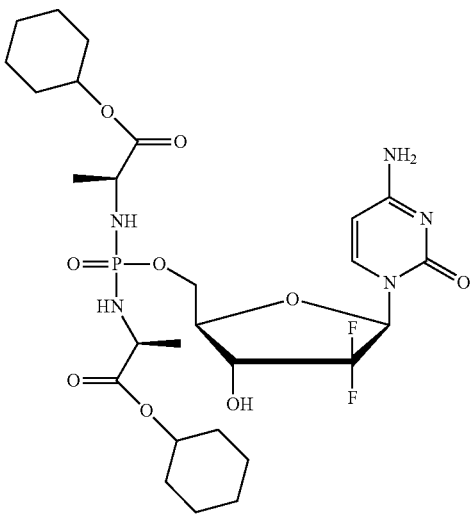

$C_{27}H_{42}F_2N_5O_9P$
Molecular Weight: 649.62 g/mol

Prepared according to the standard procedure B from Gemcitabine (0.25 g, 0.95 mmol), POCl$_3$ (0.29 g, 0.17 mL, 1.89 mmol), and (Et)$_3$PO (1.0 mL), followed by addition of L-Ala cyclohexyl ester HCl salt (0.99 g, 4.75 mmol), DIPEA (1.23 g, 1.65 mL, 9.50 mmol). Column purification followed by preparative TLC purification gave the product 4 as a white solid (0.029 g, 5%).

$^{31}$P-NMR (MeOD, 202 MHz) δ 13.94

$^{19}$F-NMR (MeOD, 121 MHz) δ −118.30 (d, J=241 Hz), −119.78 (d, broad signal, J=245 Hz)

$^{1}$H-NMR (MeOD, 500 MHz) δ 7.70 (1H, d, J=7.15 Hz, H-base), 6.29 (1H, t, J=7.97 Hz, H-1'), 6.01 (1H, d, J=7.51 Hz, H-base), 4.79-4.73 (2H, m, 2×CH-cyclohexyl), 4.37-4.33 (1H, m, H-5'), 4.32-4.22 (2H, m, H-3', H-5'), 4.08-4.06 (1H, m, H-4'), 3.93-3.89 (2H, m, 2×CHCH$_3$), 1.87-1.84 (4H, m, 2×CH$_2$, cyclohexyl), 1.77-1.74 (4H, m, 2×CH$_2$, cyclohexyl), 1.58-1.56 (2H, m, 2×CH of CH$_2$-cyclohexyl), 1.48-1.33 (16H, m, 10H, CH$_2$-cyclohexyl; 6H, 2×CHCH$_3$)

$^{13}$C-NMR (MeOD, 125 MHz) δ 175.64 (d, $^3J_{C—P}$=5.37 Hz, C=O, ester), 167.69 (C=O, C—Ar, base), 157.79 (C—Ar, base), 142.66 (CH—Ar, base), 123.66 (apparent t, $^1J_{C—F}$=259 Hz, CF$_2$), 96.85 (CH—Ar, base), 86.00 (apparent t, broad signal, $^2J_{C—F}$=30 Hz, C-1'), 80.48 (apparent t, $^3J_{C—F}$=8.50 Hz, C-4'), 74.66, 74.56 (2×CH-cyclohexyl), 71.29 (apparent t, $^2J_{C—F}$=25.0 Hz, C-3'), 64.54 (d, $^2J_{C—P}$=4.23 Hz, C-5'), 51.13 (d, $^2J_{C—P}$=13.0 Hz, CHCH$_3$), 32.55, 32.53, 32.48, 32.34, 26.58, 26.44, 24.79, 24.69 (CH$_2$-cyclohexyl), 21.15, 20.93 (2×d, $^3J_{C—P}$=5.52 Hz, CHCH$_3$)

MS (ES+) m/e: 672.26 (MNa$^+$, 100%), Accurate mass: $C_{27}H_{42}F_2N_5O_9P$ required 649.62 found 650.28 (33%)

HPLC$_b$ (H$_2$O/CH$_3$CN from 100/0 to 0/100 in 35 min) Rt 17.72 min

2'-Deoxy-2',2'-difluoro-D-cytidine-5'-O-bis(2,2-dimethylpropoxy-L-alaninyl)]-phosphate (5, CPF460)

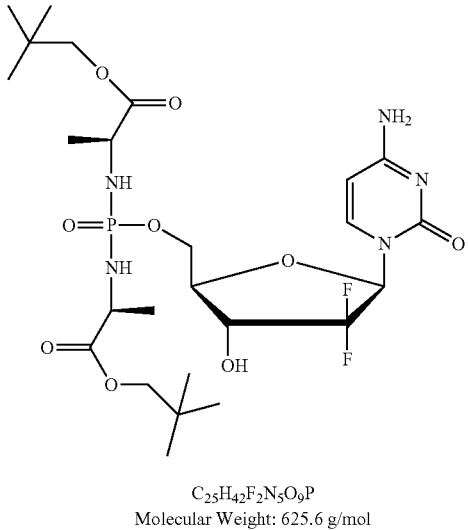

$C_{25}H_{42}F_2N_5O_9P$
Molecular Weight: 625.6 g/mol

Prepared according to the standard procedure B from Gemcitabine (0.25 g, 0.95 mmol), POCl$_3$ (0.29 g, 0.17 mL, 1.89 mmol), and (Et)$_3$PO (1.0 mL), followed by addition of L-Ala neopentyl ester Ts salt (1.57 g, 4.75 mmol), DIPEA (1.23 g, 1.65 mL, 9.50 mmol). Column purification followed by preparative TLC purification gave the compound 5 as a white solid (0.041 g, 7%).

$^{31}$P-NMR (MeOD, 202 MHz) δ 13.93
$^{19}$F-NMR (MeOD, 121 MHz) δ −118.1 (d, J=245 Hz), −119.6 (d, J=245 Hz)
$^{1}$H-NMR (MeOD, 500 MHz) δ 7.70 (1H, d, J=7.58 Hz, H-base), 6.29 (1H, t, J=8.20 Hz, H-1'), 6.01 (1H, d, J=7.58 Hz, H-base), 4.37-4.33 (1H, m, H-5'), 4.30-4.23 (2H, m, H-5', H-3'), 4.08-4.06 (1H, m, H-4'), 4.03-3.96 (2H, m, 2×CHCH$_3$), 3.90, 3.93, 3.79, 3.73 (4H, 2×AB, J$_{AB}$=10.55 Hz, 2×CH$_2$C(CH$_3$)$_3$), 1.45, 1.43 (6H, 2×d, J=7.08 Hz, 2×CHCH$_3$), 0.97 (18H, s, 2×CH$_2$C(CH$_3$)$_3$)
$^{13}$C-NMR (MeOD, 125 MHz) δ 175.71, 175.67 (2×d, $^3J_{C-P}$=3.44 Hz, C=O, ester), 167.70 (C=O, C—Ar, base), 157.79 (C—Ar, base), 142.68 (CH—Ar, base), 123.65 (apparent t, $^1J_{C-F}$=258 Hz, CF$_2$), 96.84 (CH—Ar, base), 86.04 (apparent t, $^2J_{C-F}$=26 Hz, C-1'), 80.48 (apparent t, $^3J_{C-F}$=8.51 Hz, C-4'), 75.46, 75.43 (CH$_2$C(CH$_3$)$_3$), 71.30 (t, $^2J_{C-F}$=23.0 Hz, C-3'), 64.57 (d, $^2J_{C-P}$=4.73 Hz, C-5'), 51.17 (d, $^2J_{C-P}$=7.78 Hz, CHCH$_3$), 26.7 (CH$_2$C(CH$_3$)$_3$), 21.08, 20.96 (2×d, $^3J_{C-P}$=6.10 Hz, CHCH$_3$)

MS (ES+) m/e: 648 (MNa$^+$, 100%), Accurate mass: C$_{25}$H$_{42}$F$_2$N$_5$O$_9$P required 625.60. found 626.28 (2%)
HPLC$_b$ (H$_2$O/CH$_3$CN from 100/0 to 0/100 in 35 min) Rt 17.27 min

2'-Deoxy-2',2'-difluoro-D-cytidine-5'-O-bis(iso-propoxy-L-alaninyl)]phosphate (6, CPF461)

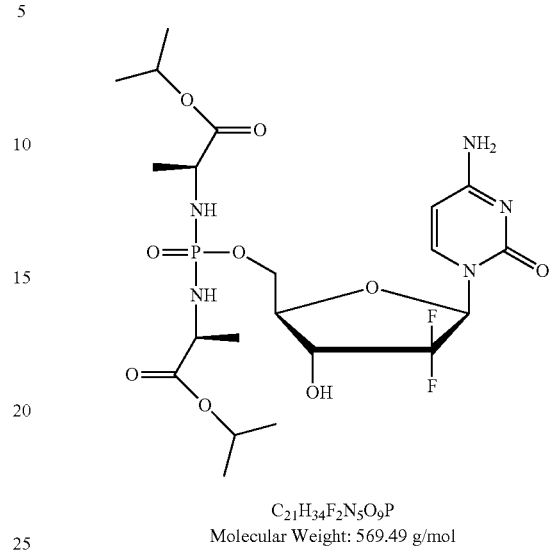

$C_{21}H_{34}F_2N_5O_9P$
Molecular Weight: 569.49 g/mol

Prepared according to the standard procedure B from Gemcitabine (0.25 g, 0.95 mmol), POCl$_3$ (0.29 g, 0.17 mL, 1.89 mmol), and (Et)$_3$PO (1.0 mL), followed by addition of L-Ala isopropyl ester HCl salt (0.80 g, 4.75 mmol), DIPEA (1.23 g, 1.65 mL, 9.50 mmol). Column purification followed by preparative TLC purification gave the product 6 as a white solid (0.037 g, 7%).

$^{31}$P-NMR (MeOD, 202 MHz) δ 13.97
$^{19}$F-NMR (MeOD, 121 MHz) δ −117.5 (d, J=245 Hz), −120.3 (d, J=245 Hz)
$^{1}$H-NMR (MeOD, 500 MHz) δ 7.70 d, J=7.20 Hz, H-base), 6.29 (1H, t, J=8.0 Hz, H-1'), 6.00 (1H, d, J=7.20 Hz, H-base), 5.10-4.98 (2H, apparent septet, J=6.40 Hz, 2×H, CH(CH$_3$)$_2$), 4.36-4.34 (1H, m, H-5'), 4.30-4.22 (2H, m, H-5', H-3'), 4.09-4.06 (1H, m, H-4'), 3.93-3.86 (2H, m, 2×H, CHCH$_3$), 1.49, 1.47 (6H, 2×d, J=6.70 Hz, 2×CHCH$_3$), 1.29-1.26 (12H, m, 2×CH(CH$_3$)$_2$)
$^{13}$C-NMR (MeOD, 125 MHz) δ 175.25 (d, J$_{C-P}$=2.20 Hz, C=O, ester), 167.70 (C=O, C—Ar, base), 157.81 (C—Ar, base), 142.68 (CH—Ar, base), 123.38 (apparent t, $^1J_{C-F}$=257 Hz, CF$_2$), 96.85 (CH—Ar, base), 85.94 (apparent t, $^2J_{C-F}$=28.7 Hz, C-1'), 80.46 (apparent t, $^3J_{C-F}$=8.21 Hz, C-4'), 71.28 (apparent t, $^2J_{C-F}$=24.0 Hz, C-3'), 70.12 (CH(CH$_3$)$_2$), 64.52 (d, $^2J_{C-P}$=4.77 Hz, C-5'), 51.17 (d, $^2J_{C-P}$=8.6 Hz, CHCH$_3$), 22.07, 22.05 (CH(CH$_3$)$_2$), 20.91, 20.82 (2×d, $^3J_{C-P}$=6.3 Hz, CHCH$_3$)

MS (ES+) m/e: 592.19 (MNa$^+$, 100%), Accurate mass: C$_{21}$H$_{34}$F$_2$N$_5$O$_9$P required 569.49. found 570.20 (10%)
HPLC$_b$ (H$_2$O/CH$_3$CN from 100/0 to 0/100 in 35 min) Rt 12.15 min Biological assay.

Human colon cancer cell line HRT18 were purchased from the European Collection of Animal Cell Cultures (ECACC, Salisbury, England). Cytoxicity assay was based on MTT assay as we previously reported. The method is based on the ability of viable mitochondria to convert MTT, a soluble tetrazolium salt (3-[4,5-dimethylthiazd-2-yl]-2,5-diphenyltetrazolium bromide) into an insoluble formazan precipitate that is dissolved and quantified by spectrophotometry. A 96-well culture cell culture plate was used. Cells were counted with a haemocytomete counting chamber and a specific number (4000 per well) of cells were seeded to each well with culture medium (DMEM). Compounds, dissolved in DMSO, were series diluted (1:5) in culture medium, to cover a final concentration range between 0.128 and 2000 nM. The culture plate was incubated for 72 h at 37° C. The cells were washed twice with BSS. A solution of MTT in 0.5 mg/mL in culture medium was added into each well. The culture plate was then incubated at 37° C. for 4 h. MTT was then removed by aspiration. The crystals produced by MTT reagent within the cells were then extracted by the addition of 100 1L of Triton X100 (10% in water). The cells were incubated at 4° C. for 24 h. The absorbance of the colorimetric products was then measured at a wavelength of 540 nm using a spectrophotometer (Titertecek).
Data:

| Cpd L-Ala Gemcitabine diamidate ($R_7$) | EC50 (nM) Colorectal cell HRT18 |
| --- | --- |
| CPF457 Bn | 14 |
| CPF458 cycHex | 31 |
| CPF459 Et | 42 |
| CPF460 CH2tBu | 1.6 |
| CPF461 iPr | 3.2 |
| Gemcitabine | 64 |

It can be observed that all of the diamidates are more potent than gemcitabine parent in this assay; some are up to 20 times more potent. Potency varies with the group $R_7$ of the ester as shown in the table, and also with the amino moiety (data not shown).

I claim:

1. A chemical compound having formula I:

[I]

wherein:
   $R_2$ is selected from $CR_5R_6CO_2R_7$ and $C_1$-$C_6$ alkyl and $R_1$ is selected from H and $C_1$-$C_6$ alkyl, or $R_1$ and $R_2$ together with the N atom to which they are attached form a ring moiety consisting of 5 to 8 ring atoms;
   $R_4$ is selected from $CR_5R_6CO_2R_7$ and $C_1$-$C_6$ alkyl and $R_3$ is selected from H and $C_1$-$C_6$ alkyl, or $R_3$ and $R_4$ together with the N atom to which they are attached form a ring moiety consisting of 5 to 8 ring atoms;
   where, independently for each of $R_2$ and $R_4$:
   $R_5$ and $R_6$ are selected, independently, from the side chains of naturally occurring alpha amino acids;
   $R_7$ is selected from $C_1$-$C_{18}$ alkyl;
   Y is selected from H and C(O)R, where R is $C_1$-$C_{18}$ alkyl; and
   Z is selected from H and C(O)R, where R is $C_1$-$C_{18}$ alkyl, or a pharmaceutically acceptable salt or crystalline form of a compound of formula I.

2. The compound according to claim 1, or a pharmaceutically acceptable salt or crystalline form of said compound, where $R_2$ and $R_4$ are the same.

3. The compound according to claim 1, or a pharmaceutically acceptable salt or crystalline form of said compound, where $R_2$ and $R_4$ are each $CR_5R_6CO_2R_7$.

4. The compound according to claim 1, or a pharmaceutically acceptable salt or crystalline form of said compound, wherein $R_7$ is selected from branched and unbranched, substituted or unsubstituted, and saturated or unsaturated $C_1$-$C_{18}$ acyclic alkyl and $C_3$-$C_8$ cyclic alkyl.

5. The compound according to claim 4, or a pharmaceutically acceptable salt or crystalline form of said compound, wherein $R_7$ is selected from methyl, ethyl, i-propyl, t-butyl-$CH_2$—, benzyl and $C_3$-$C_6$ cycloalkyl.

6. The compound according to claim 5, or a pharmaceutically acceptable salt or crystalline form of said compound, where $R_7$ is t-butyl-$CH_2$—.

7. The compound according to claim 1, or a pharmaceutically acceptable salt or crystalline form of said compound, wherein $R_6$ is H and $R_5$ is selected from the side chains of naturally occurring alpha amino acids.

8. The compound according to claim 7, or a pharmaceutically acceptable salt or crystalline form of said compound, wherein $R_6$ is H and $R_5$ is selected from H, methyl, i-propyl, —$CH_2Ph$, —$CH_2CH(CH_3)_2$ and —$CH(CH_3)(C_2H_5)$.

9. The compound according to claim 8, or a pharmaceutically acceptable salt or crystalline form of said compound, wherein $R_6$ is H and $R_5$ is methyl.

10. The compound according to claim 9, or a pharmaceutically acceptable salt or crystalline form of said compound, wherein $R_7$ is selected from methyl, ethyl, i-propyl, t-butyl-$CH_2$—, benzyl and $C_3$-$C_6$ cycloalkyl.

11. The compound according to claim 10, or a pharmaceutically acceptable salt or crystalline form of said compound, wherein $R_7$ is t-butyl-$CH_2$—.

12. The compound according to claim 1, or a pharmaceutically acceptable salt or crystalline form of said compound, where the compound has natural L stereochemistry at *$CR_5R_6$.

13. The compound according to claim 1, or a pharmaceutically acceptable salt or crystalline form of said compound, wherein the compound has D stereochemistry at *$CR_5R_6$.

14. The compound according to claim 1, or a pharmaceutically acceptable salt or crystalline form of said compound, wherein each of $R_5$ and $R_6$ is methyl.

15. The compound according to claim 1, or a pharmaceutically acceptable salt or crystalline form of said compound, wherein each of $R_1$ and $R_3$ is the same.

16. The compound according to claim 15, or a pharmaceutically acceptable salt or crystalline form of said compound, wherein each of $R_1$ and $R_3$ is H.

17. The compound according to claim 16, or a pharmaceutically acceptable salt or crystalline form of said compound, wherein each of $R_1$ and $R_3$ is H and each of $R_2$ and $R_4$ is $CR_5R_6CO_2R_7$.

18. The compound according to claim 17, or a pharmaceutically acceptable salt or crystalline form of said compound, wherein each of $R_1$ and $R_3$ is H and each of $R_2$ and $R_4$ is $CR_5R_6CO_2R_7$ wherein $R_6$ is H and $R_5$ is selected from the side chains of naturally occurring alpha amino acids.

19. The compound according to claim 18, or a pharmaceutically acceptable salt or crystalline form of said compound, wherein $R_5$ is selected from H, methyl, i-propyl, —CH$_2$Ph, —CH$_2$CH(CH$_3$)$_2$ and —CH(CH$_3$)(C$_2$H$_5$).

20. The compound according to claim 19, or a pharmaceutically acceptable salt or crystalline form of said compound, wherein $R_7$ is selected from the group consisting of methyl, ethyl, i-propyl, t-butyl-CH$_2$—, benzyl and C$_3$-C$_6$ cycloalkyl.

21. The compound according to claim 1, or a pharmaceutically acceptable salt or crystalline form of said compound, wherein $R_1$ and $R_2$ together with the N atom to which they are attached form a ring moiety consisting of 5 to 8 ring atoms and $R_3$ and $R_4$ together with the N atom to which they are attached form a ring moiety consisting of 5 to 8 ring atoms.

22. The compound according to claim 1, or a pharmaceutically acceptable salt or crystalline form of said compound, wherein each of Y and Z is H.

23. A method of treatment of cancer selected from colon cancer, breast cancer, pancreatic cancer, lung cancer and prostate cancer, comprising administering to a patient in need of such treatment an effective dose of a compound according to claim 1, or a pharmaceutically acceptable salt or crystalline form of said compound.

24. A pharmaceutical composition comprising a compound according to claim 1, or a pharmaceutically acceptable salt or crystalline form of said compound, in combination with a pharmaceutically acceptable carrier, diluent or excipient.

25. A method of preparing a pharmaceutical composition comprising the step of combining a compound according to claim 1, or a pharmaceutically acceptable salt or crystalline form of said compound, with a pharmaceutically acceptable excipient, carrier or diluent.

26. A process for preparing a compound of formula I according to claim 1, the process comprising reacting with phosphoryl chloride (POCl$_3$) a compound of formula (II):

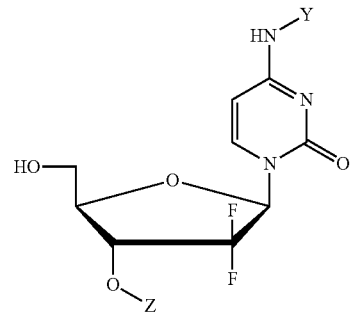

followed by reaction with R$_1$R$_2$NH and R$_3$R$_4$NH
wherein
R$_1$, R$_2$, R$_3$, R$_4$, R$_5$, R$_6$, R$_7$, R, Y, and Z have the meanings described in claim 1, wherein when Z is H, the 3'-OH is pre-protected prior to reaction with the POCl$_3$ and deprotected after reaction with R$_1$R$_2$NH and R$_3$R$_4$NH.

27. A compound selected from the group consisting of:
2'-deoxy-2',2'-difluoro-D-cytidine-5'O-bis(ethoxy-L-alaninyl)-phosphate;
2'-deoxy-2',2'-difluoro-D-cytidine-5'O-bis(benzoxy-L-alaninyl)-phosphate;
2'-deoxy-2',2'-difluoro-D-cytidine-5'O-bis(cyclohexoxy-L-alaninyl)-phosphate;
2'-deoxy-2',2'-difluoro-D-cytidine-5'O-bis(2,2-dimethyl-propoxy-L-alaninyl)-phosphate; and
2'-deoxy-2',2'-difluoro-D-cytidine-5'O-bis(iso-propoxy-L-alaninyl)-phosphate, or a pharmaceutically acceptable salt or crystalline form of said compound.

* * * * *